(12) United States Patent
Lagercrantz et al.

(10) Patent No.: US 8,211,090 B2
(45) Date of Patent: Jul. 3, 2012

(54) HEART TRACKING DEVICE

(75) Inventors: Per Lagercrantz, Stockholm (SE); Kenth Nilsson, Åkersberga (SE)

(73) Assignee: St. Jude Medical AB, Jarfalla (SE)

( * ) Notice: Subject to any disclaimer, the term of this patent is extended or adjusted under 35 U.S.C. 154(b) by 301 days.

(21) Appl. No.: 11/916,414

(22) PCT Filed: Jun. 29, 2005

(86) PCT No.: PCT/SE2005/001028
§ 371 (c)(1),
(2), (4) Date: Dec. 6, 2008

(87) PCT Pub. No.: WO2007/001217
PCT Pub. Date: Jan. 4, 2007

(65) Prior Publication Data
US 2009/0137932 A1 May 28, 2009

(51) Int. Cl.
*A61M 25/00* (2006.01)
*A61B 5/00* (2006.01)

(52) U.S. Cl. ........ 604/528; 600/585; 604/523; 604/525; 604/532

(58) Field of Classification Search ............... 600/373, 600/585; 604/95.01, 95.02, 264, 523, 525, 604/528, 532, 534
See application file for complete search history.

(56) References Cited

U.S. PATENT DOCUMENTS

| | | | | |
|---|---|---|---|---|
| 3,773,034 A * | 11/1973 | Burns et al. | | 600/434 |
| 4,403,985 A * | 9/1983 | Boretos | | 604/528 |
| 4,906,230 A * | 3/1990 | Maloney et al. | | 604/95.03 |
| 4,909,787 A * | 3/1990 | Danforth | | 604/95.03 |
| 4,920,967 A | 5/1990 | Cottonaro et al. | | |
| 5,484,407 A * | 1/1996 | Osypka | | 604/95.04 |
| 5,619,993 A * | 4/1997 | Lee | | 600/373 |
| 5,728,148 A | 3/1998 | Boström et al. | | |
| 5,897,536 A * | 4/1999 | Nap et al. | | 604/524 |
| 5,902,287 A * | 5/1999 | Martin | | 604/532 |
| 6,165,123 A * | 12/2000 | Thompson | | 600/152 |
| 6,443,912 B1 | 9/2002 | Mazzola et al. | | |
| 7,101,362 B2 * | 9/2006 | Vanney | | 604/523 |
| 2001/0001809 A1 | 5/2001 | Berg et al. | | |
| 2002/0013540 A1 | 1/2002 | Jacobsen et al. | | |
| 2004/0186378 A1 * | 9/2004 | Gesswein | | 600/435 |
| 2005/0159725 A1 * | 7/2005 | Tockman et al. | | 604/500 |

FOREIGN PATENT DOCUMENTS

WO WO 96/38196 12/1996

* cited by examiner

Primary Examiner — Max Hindenburg
Assistant Examiner — Devin Henson

(57) ABSTRACT

A vessel tracking device for use with a pressure source has an elongate introduction element configured for introduction into a vessel of a human body, the introduction element having a proximal end and a distal end, and the distal end having a flexible distal end portion containing an internal cavity that is closed at the distal end. A pressure adjuster is configured for communication with said pressure source. The introduction element has a connection channel connected to the pressure adjuster at the proximal end of the introduction element, the connection channel being connected with the internal cavity and placing the internal cavity in communication with the pressure source, with the pressure adjuster controlling an internal pressure in the internal cavity. The distal end portion has different wall portions that are differently deformed as the internal pressure is adjusted, to produce a change in direction of the distal end controlled by the pressure controller.

17 Claims, 2 Drawing Sheets

HEART TRACKING DEVICE

BACKGROUND OF THE INVENTION

1. Field of the Invention

The present invention relates to a vessel tracking device, which is introducible into a vessel of a human body.

2. Description of the Prior Art

When an elongate unit, such as for example a pacemaker lead, is going to be introduced into a vessel of the human body for temporary or permanent placement it is often preferable to use an aid for guiding the unit. A vessel tracking device is used for tracking vessels until a front end, or distal end, of the device reaches a predetermined destination. Then the very elongate unit can be introduced guided by the vessel tracking device. When introducing the device, typically, tricky passages are reached where it is difficult to go ahead. In order to facilitate such passages, a distal end portion being one or a few centimeters long, is often prebent. On the other hand such a prebend can cause problems when a vessel is narrowing.

U.S. Pat. No. 5,728,148 discloses a stylet unit where the bend of the distal end portion is variable by remote control thereof. The stylet unit has coaxially arranged stylet elements, consisting of a tubular stylet sleeve and an internal stylet, which is movable back and forth within the sleeve. A distal end portion of the stylet is prebent to a great extent, while the sleeve is straight. When, during the introduction of the stylet unit into a vessel, a straight distal end portion is desirable, the stylet is retracted into the sleeve, and when a bend is desirable the stylet is pushed out of the sleeve. This prior art vessel tracking device is unnecessary difficult to manoeuvre, since when moving the stylet along the sleeve the distal end thereof is moved in relation to the vessel. Thus the stylet movement has to be compensated for by counter movement of the sleeve.

SUMMARY OF THE INVENTION

It is an object of the present invention to provide a vessel tracking device that is easier to handle than the prior art stylet unit while keeping the ability of remotely controlling the bending of the distal end portion.

This object is achieved by a vessel tracking device in accordance with the present invention, there is provided a vessel tracking device having an elongate introduction element, which has a proximal end and a distal end, and which is introducible into a vessel of a human body. The introduction element has a flexible distal end portion including an internal cavity. The internal cavity is closed at the distal end. The introduction element further comprises a connection channel, which is connectable to a pressure adjustment means, at the proximal end of the introduction element. The connection channel, in turn, is connected with the internal cavity of the distal end portion for controlling an internal pressure thereof. The distal end portion comprises different wall portions which are differently deformed when the internal pressure is changed, thereby causing a change in the direction of said distal end.

Thus, in the device according to the invention, the distal end portion is bendable by means of pressure changes. For example, the end portion can be preformed and then bent more by means of decreasing the internal pressure and bent less by increasing the pressure, or it can be initially straight and bent either by increasing or decreasing the pressure, etc. It is to be noted that in different embodiments, the deformation of the wall portions can be either longitudinal or radial or a combination thereof. The distal end of this vessel tracking device is not pushed or pulled when the bending thereof is changed, thereby being easier to operate than the known stylet unit described above.

In accordance with an embodiment of the device, the distal end portion changes its cross sectional shape when the internal pressure is changed. For example, if the cross section is elliptic, the ratio of the shortest diameter to the longest diameter is changed.

In accordance with an embodiment of the device, the distal end portion and the internal cavity are elliptical. The ellipses have the same orientation and the distal portion is prebent in a first longitudinal plane and has a smaller outer diameter in that plane than in a plane orthogonal thereto. Consequently, when the pressure is raised in the internal cavity the distal end portion is inflated and straightened at the same time. The raising pressure forces the distal end portion to change its shape towards a more circular cross-section.

In accordance with another embodiment of the device, said smaller outer diameter decreases towards the distal end. In other words, the distal end portion is most flat at the distal end and less flat further away from the distal end. Thus, for a particular pressure adjustment, the bend of the distal end portion changes most at the distal end of the internal cavity.

In accordance with another embodiment of the device, the different wall portions each has a different modulus of elasticity. Then, a pressure change will cause different extension/contraction in the different wall portions, which in turn result in a change in the bend of the distal end portion. The different modulus of elasticity can, for example, be obtained by means of different materials in the different wall portions.

In accordance with another embodiment of the device, the bending control is obtained by the internal cavity extending eccentrically relative to the longitudinal centre axis of the distal end portion. That is, the longitudinal center axis of the internal cavity does not coincide with the longitudinal center axis of the distal end portion as a whole. Consequently, there are opposite wall portions which have different thickness and will thus be differently deformed when the internal pressure is changed.

In an embodiment of the device, it forms a pacemaker lead. Thus, the inventive bending control is implemented directly in a pacemaker lead, thereby substantially facilitating the introduction thereof into a body.

In accordance with another aspect of the present invention, there is provided an apparatus for guiding the introduction of an elongate unit into a human body. For instance the elongate unit can be a pacemaker lead. The vessel tracking device is then completed with a guidance sleeve. The guidance sleeve is slid along the device on the outside thereof, for example after the device has been introduced into a vessel, as is defined by a method according to this invention.

Thus, according to another aspect of this invention, there is provided a method for introducing a guidance sleeve into a body cavity of a human body. The remotely controllable bending of the distal end portion facilitates the passage of the distal end into branching vessels, etc.

DESCRIPTION OF THE PREFERRED EMBODIMENTS

Figure 1:
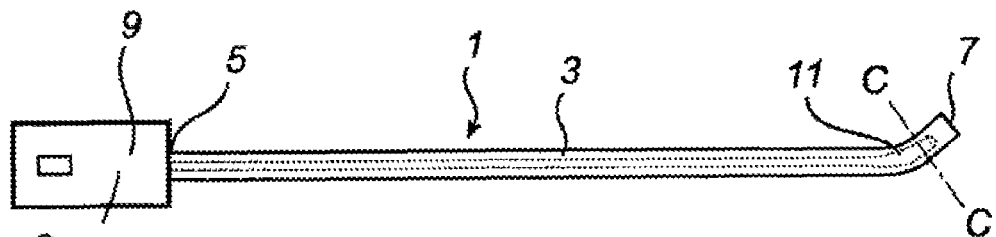
FIG. 1 schematically shows an embodiment of a device according to the present invention.

An embodiment of the vessel tracking device 1 has an introduction element 3, having a proximal end 5 and a distal end 7, and a pressure adjustment means, or pressure controller, 9. The introduction element 3 is elongate and the pressure controller 9 is connected to the proximal end 5 of the introduction element 3. The introduction element 3 has a distal end portion 11, which is flexible and includes a longitudinal internal cavity 13. Thus, the distal end portion 11 constitutes a tube which is closed at one end. The internal cavity 13 is defined by a surrounding wall 14, and more particularly, by an inner surface of the wall 14. The internal cavity 13 does not fully reach the end surface of distal end 7, but is closed at that end. The internal cavity 13 narrows toward the proximal end 5, at a transition portion 15 between the distal end portion 11 and the rest of the introduction element 3, and then extends, as a thin communication channel 17 to the proximal end 5. The pressure controller 9 is connected to the communication channel 17 for adjusting the internal pressure of the internal cavity 13. Thus, by means of forcing additional medium into the communication channel 17 the pressure is increased, and by evacuating medium of the communication channel 17 the pressure is decreased. Preferably, the medium is a liquid, such as physiological saline solution or liquid silicone.

The distal end portion 11 is designed such that pressure changes causes bending thereof. There are several possible designs that work, and some of them will be described below.

Figure 2A:
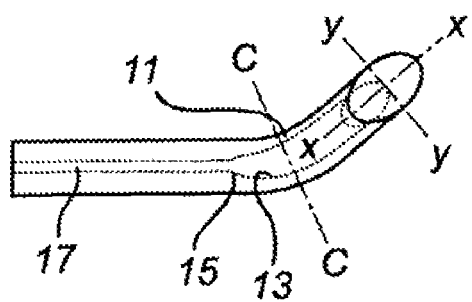
FIGS. 2a-2d schematically show portions of different elliptic embodiments of the device.
Figure 2B:
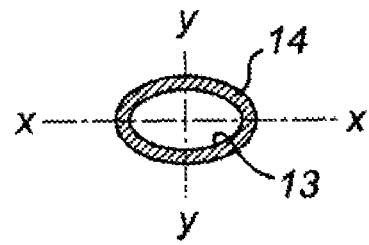
Figure 2C:
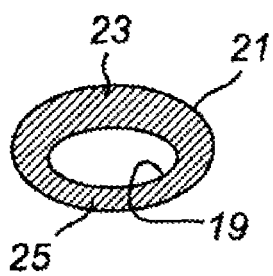
Figure 2D:
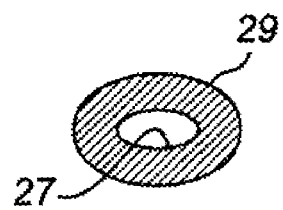

In FIGS. 2a-2d, elliptic embodiments are shown. More particularly, in FIGS. 2a and 2b the circumference of the distal end portion 11, or the cross-section of the outer wall surface thereof, is elliptical, and the circumference of the internal cavity 13, or the inner wall surface of the wall 14, is elliptic as well. The internal cavity 13 is centered in the distal end portion 11, i.e. the internal cavity 13 is concentric with the distal end portion 11 as a whole. Further, the internal cavity 13 is rotationally aligned with the outer ellipse. In other words, the largest diameter, along the X-axis as shown in FIG. 2a, of the channel coincides with the largest outer diameter of the distal end portion 11. Their smallest diameters, along the Y-axis in FIG. 2a, coincide as well. The distal end portion 11 is prebent, i.e. bent in advance, to a certain extent. The bend is in a longitudinal plane wherein the Y-axis resides.

Figure 7:
FIG. 7 schematically shows bending an end portion of the device more or less.
Figure 8:
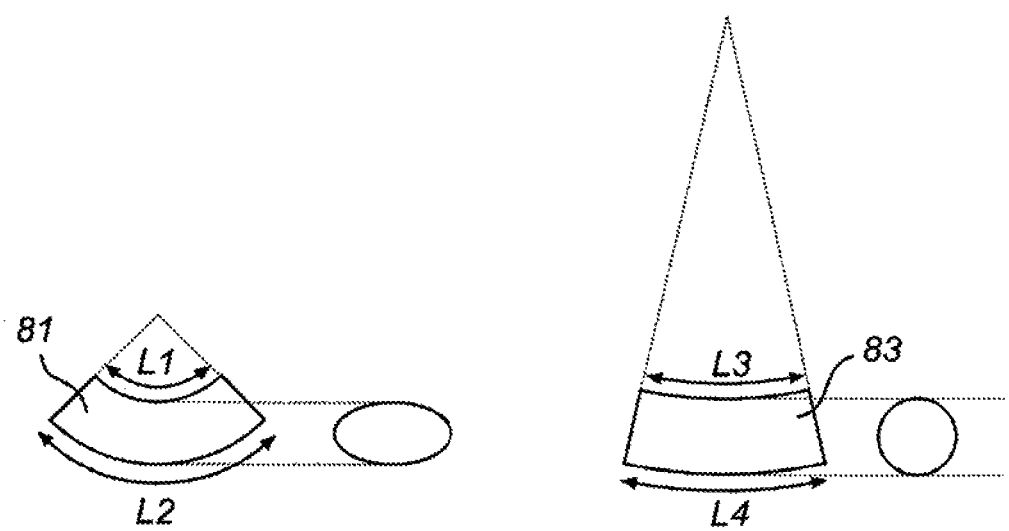
FIG. 8 schematically shows the principle of pressure controlled bending.

When the pressure controller 9 is operated to increase the pressure of the internal cavity 13, since the distal end portion 11 is flexible, the cross-sectional shape of the distal end portion 1 is changed. The internal cavity 13 assumes a more circular shape, thereby causing an increase of the bending radius, as shown in FIG. 7, i.e. the distal end portion 11 straightens to an extent that is dependent on the amount of the pressure increase. FIG. 8 shows a section 81 of the distal end portion 11 projected onto a plane such that the bend is in the plane. For a bent tube having a uniform wall thickness, the difference in length between the length L1 of an inner curve of the section 81 and the length 2 of an outer curve of the section 81 strives to remain constant when the elliptical shape is changed due to the pressure change. Thus, when the shape becomes more circular, the distance between the inner and outer curves is increased, resulting in a straightening of the tube in order to keep the difference in length, i.e. L2-L1, constant. The connection channel 17 between the internal cavity 13 and the proximal end 5 has a substantially smaller diameter than the internal cavity. The connection channel 17 is thin enough not to cause any significant dimensional changes of the surrounding wall when the pressure is changed.

Further, the ellipse should be as flat as possible in order to achieve as large change of the radius of the bend as possible for a given pressure change.

In another embodiment the internal cavity 19 is not concentrically but eccentrically located. Consequently, the surrounding wall 21 has a non-uniform thickness, such that a thicker wall portion, or section, 23 is opposite of a thinner wall section 25. If the distal end portion is prebent such that the thicker wall section 23 forms the outer curve and the thinner wall forms the inner curve, the bending effect of the pressure adjustments is, enhanced. This is because the thinner wall section 25 is more easily stretched than the thicker wall section 23, and consequently they are differently deformed.

In another embodiment the elliptic shape of the inner cavity 27 differs from the elliptical shape of the outer circumference 29 of the distal end portion, i.e. the ratio of the smallest diameter to the largest diameter of the cross-section of the internal cavity 27 differs from the corresponding ratio of the shape of the outer circumference 29.

Figure 3:
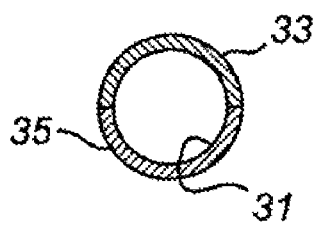
FIGS. 3-5 schematically show cross-sections of other embodiments of the device.

In another embodiment, as shown in FIG. 3, the distal end portion is circular in cross-section, and so is an internal cavity 31 thereof, and has a wall 33, 35 of uniform thickness. However, one half 33 of the wall of the tubular distal end portion is made of a different material than the other half 35 of the wall, the different materials each having a different modulus of elasticity. Consequently, when filling or evacuating the inner channel 31 the wall halves extend or retract unequally, thereby causing a change in direction of the distal end, i.e. a change in the bending of the distal end portion. In this embodiment as well as in some other embodiments the basic shape of the distal end portion can be straight, and still it will bend when the internal pressure is changed. As an alternative to different materials, one of the wall portions/halves can be reinforced.

Figure 4:
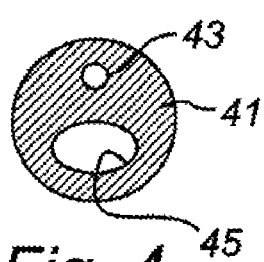

In another embodiment as shown in FIG. 4, the distal end portion 41 is provided with a further internal cavity 43, which extends throughout the introduction element and which will also be called wire lumen in the following. The wire lumen is used for admitting a thin wire into and through the introduction element. The use of this wire will be further explained below. In this embodiment the internal cavity 45 for pressure control is eccentrically located. The cross-sectional shapes are circular, but the distal end portion 41 and the internal cavity 45 could be 25 elliptic as well, while the wire lumen 43 is better if circular. Again, due to differently thick wall sections on opposite sides of the internal cavity 45 the bending at pressure changes is obtained.

Figure 5:
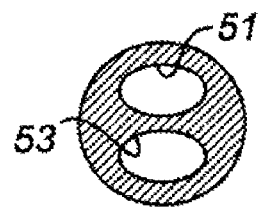

In another embodiment as shown in FIG. 5, there are two internal cavities for pressure control. The pressure controller 9 has two different operation levers, each for individually operating the internal pressure of a respective one of the internal cavities.

Figure 6:
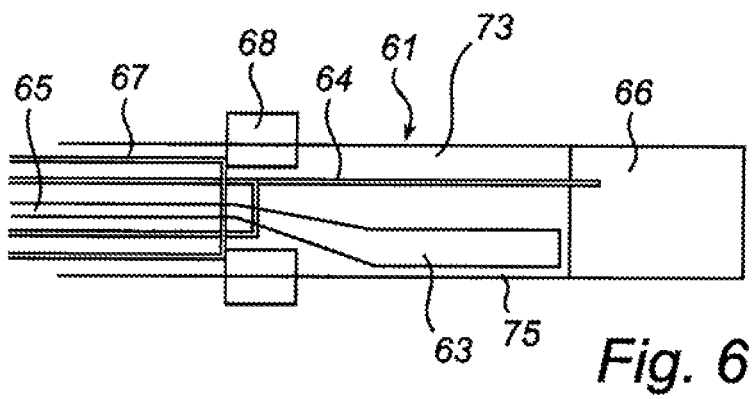
FIG. 6 schematically shows a portion of another embodiment of the device.

In another embodiment of the device, as illustrated in FIG. 6, it is a pacemaker lead. The internal cavity 63 of the distal end portion 61 extends eccentrically and the connection channel 65 extends concentrically. A portion of the internal cavity 63 adjacent to the connection channel 65 extends non-parallel with the centre axis of the introduction element 69. In this embodiment a first electrode coil 64, extending concentric with and outside of the connection channel 65, is narrowed and offset in the distal end portion 61 and is connected with an end electrode 66 of the lead. Thus, in the distal end portion 61 a thicker wall section 73 and a thinner wall section 75 are formed on opposite sides of the internal cavity 63. The electrode coil 71 is located to the thicker wall section 73 and serves as a reinforcement of the thicker wall section 73. The reinforcement enhances the effect of the pressure controlled bending. A second electrode coil extending concentric with and outside of the connection channel 65, is connected with a second electrode 68 arranged as a ring at a proximal end of the distal end portion 61.

Figure 9:
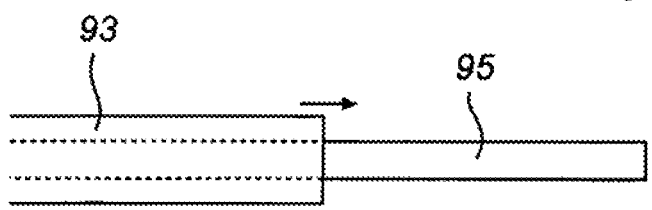
FIG. 9 schematically illustrates an embodiment of a method according to the present invention.

Referring now to FIG. 9, an embodiment of an apparatus for guiding the introduction of an elongate unit into a human body, consists of the vessel tracking device and an elongate guidance sleeve 93. The guidance sleeve 93 is coaxially disposable around the introduction element 95 of the vessel tracking device.

Figure 10:
FIG. 10 schematically shows a portion of another embodiment of the device.

In other embodiments of the device the distal end portion is preformed such that the radius of curvature decreases towards the distal end. In elliptical embodiments this can be obtained by flattening the distal end portion more and more toward the distal end thereof, as is illustrated in FIG. 10. For other embodiments the thickness of the wall around the internal cavity decreases toward the distal end.

Typically, the vessel tracking device is used for introducing either a guidance sleeve or a guide wire into a vessel of the human body. Additionally, as described above, the device is a pacemaker lead, which is directly introduced. First a method for introducing a guidance sleeve into a coronary vessel will be described.

The distal end 7 of the introduction element 3 is introduced into a vessel which leads to the coronary vessel. Bit by bit the introduction element 7 is fed into the vessel. When the distal end 7 reaches a difficult passage, such as a branching, where the present vessel is going to be left and a connecting vessel is to be entered, the distal end portion 11 can be steered, by means of pressure adjustments, to facilitate the entering. Then the operation lever of the pressure controller 9 is operated such that the distal end portion 11 is more bent or less bent as desired for finding the opening of the branching vessel. For example, when applying a pacemaker lead, the distal end 7 is usually introduced into a vein guiding the distal end down to the opening of the coronary sinus, which branches approximately 90 degrees from the atrial wall. For feeding the distal end 7 into the coronary sinus it is of great help to be able to bend the distal end portion 11 by means of the pressure controller 9 when the distal end 7 reaches the opening of the coronary sinus. When the distal end 7 has reached far enough into the desired final coronary vessel the pressure controller 9 is removed. If it is desirable to keep a curvature of the distal end portion 11, a valve located in the connection channel 17 at the proximal end 5 of the introduction element 3 will be closed before removing the pressure controller 9.

Then the guidance sleeve 93 will be thread on the introduction element 3, 95 at the proximal end 5 thereof, and slided along the introduction element 3, 95 towards the distal end 7 thereof until it reaches the distal end 7. Then the introduction element 3, 95 will be pulled out leaving the guidance sleeve 93 in place. The pacemaker lead will then be introduced into the guidance sleeve 93 and fed through it. Finally, the guidance sleeve 93 is pulled out leaving the pacemaker lead in place.

In another embodiment of the method, the vessel tracking device is used for introducing a guide wire, which in turn is used for introducing an instrument. Assume, for example, that a pacemaker lead is to be placed in a coronary vessel. First the introduction element 3 is introduced into the coronary vessel as just explained. In this embodiment an introduction element having a wire channel 43 has to be used. Then the pressure controller 9 is removed and a guide wire is introduced through the wire channel 43 to a position where it protrudes out of the distal end 7 of the introduction element 3. Then the introduction element 3 is pulled out and a pacemaker lead is thread over the guide wire. Finally, the guide wire is pulled out.

Alternatively, first the guide wire is placed in the introduction element and then the element is introduced into the vessel carrying the guide wire along.

Above, embodiments of the vessel tracking device and method according to the present invention have been described. These should be understood as merely non-limiting examples. As will be understood by a skilled person, many modifications and alternative embodiments are possible within the scope of the invention.

For example, the distal end portion can be S-shaped and then the eccentric positioning of the internal cavity can be alternated in order to obtain changes into or toward a straight shape or into a Z-shape from the initial S-shape.

Although modifications and changes may be suggested by those skilled in the art, it is the intention of the inventors to embody within the patent warranted heron all changes and modifications as reasonably and properly come within the scope of their contribution to the art.

We claim:

1. A vessel tracking device for use with a pressure source, comprising:
   an elongate introduction element configured for introduction into a vessel of a human body, said introduction element having a proximal end and a distal end, and said distal end comprising a flexible distal end portion having an elliptical circumference and containing an internal cavity that is closed at said distal end, said interval cavity having an elliptical cross-section in a plane containing said elliptical circumference;
   a pressure adjuster configured for communication with said pressure source;
   said introduction element also comprising a connection channel connected to said pressure adjuster at said proximal end of the introduction element, said connection channel being connected with said internal cavity and placing said internal cavity in fluid communication with said pressure source, with said pressure adjuster controlling an internal pressure in said internal cavity;
   said connection channel being concentrically located within a channel-containing portion of said introduction element, said connection channel having a smaller cross-section than said internal cavity and said channel-containing portion exhibiting substantially no dimensional change when said internal pressure is applied to said internal cavity through said connection channel; and
   said different cross-sections of said connection channel and said internal cavity causing only a part of said distal end portion in which said internal cavity is located to be deformed as said internal pressure within the internal cavity is adjusted, to produce a change in direction of only said distal end portion controlled by said pressure adjuster.

2. A vessel tracking device according to claim 1, wherein said distal end portion has a cross section that changes shape when said internal pressure is changed.

3. A vessel tracking device according to claim 1, wherein said distal end has an elliptical circumference, and wherein said internal cavity, in a transversal plane of said distal end portion, has an elliptical cross-section and has a largest diameter that is substantially parallel with a largest outer diameter of the distal end portion; and wherein said distal end portion is prebent in a first longitudinal plane and has a smaller outer diameter in said first longitudinal plane than in a second longitudinal plane orthogonal to said first longitudinal plane.

4. A vessel tracking device according to claim 3, wherein said smaller outer diameter decreases toward said distal end.

5. A vessel tracking device according to claim 3, wherein said internal cavity is concentric with the distal portion as a whole.

6. A vessel tracking device according to claim 1, wherein the distal end portion is defined by different wall portions formed in a wall defining the internal cavity, and wherein said different wall portions each has a different modulus of elasticity.

7. A vessel tracking device according to claim 6, wherein said different wall portions are made from different materials.

8. A vessel tracking device according to claim 1, wherein said internal cavity extends eccentrically relative to the longitudinal center axis of the distal end portion.

9. A vessel tracking device according to claim 8, wherein said internal cavity extends parallel to a center axis of the distal end portion as a whole.

10. A vessel tracking device according to claim 1, wherein said distal end portion includes several internal cavities, which are individually connectable to said pressure adjuster, and wherein the internal pressure of said several internal cavities is individually controllable by said pressure adjuster.

11. A vessel tracking device according to claim 10, wherein said pressure adjuster comprises several pressure adjustment members, each one being connected to a respective one of said several internal cavities.

12. A vessel tracking device according to claim 1, comprising a further internal cavity extending throughout a length of the device and being open at both ends.

13. A vessel tracking device according to claim 1, wherein the introduction element is configured to introduce a guide wire.

14. A vessel tracking device according to claim 1, wherein the introduction element is configured to introduce a pacemaker lead.

15. A vessel tracking device as claimed in claim 1 wherein said elongate introduction element is configured to introduce and guide a guide wire in said vessel.

16. A vessel tracking device as claimed in claim 1 wherein said elongate introduction element is configured to introduce and guide a pacemaker lead in said vessel.

17. A cardiac pacemaker lead comprising:
a lead body having opposite ends and terminating at one of said ends in an elongate introduction element, said lead body and said elongate introduction element being configured for introduction into a vessel of a human body;
said introduction element having a proximal end and a distal end, and said distal end comprising a flexible distal end portion having an elliptical circumference and containing an internal cavity that is closed at said distal end, said interval cavity having an elliptical cross-section in a plane containing said elliptical circumference;
a pressure adjuster configured for communication with said pressure source;
said introduction element also comprising a connection channel connected to said pressure adjuster at said proximal end of the introduction element, said connection channel being connected with said internal cavity and placing said internal cavity in fluid communication with said pressure source, with said pressure adjuster controlling an internal pressure in said internal cavity;
said connection channel being concentrically located within a channel-containing portion of said introduction element, said connection channel having a smaller cross-section than said internal cavity and said channel-containing portion exhibiting substantially no dimensional change when said internal pressure is applied to said internal cavity through said connection channel;
said different cross-sections of said connection channel and said internal cavity causing only a part of said distal end portion in which said internal cavity is located to be deformed as said internal pressure within the internal cavity is adjusted, to produce a change in direction of said distal end portion controlled by said pressure adjuster;
at least one electrical conductor proceeding through said lead body and said elongate introduction element; and
an exposed electrode located at said distal end of said introduction element and being electrically connected to said electrical conductor.

\* \* \* \* \*